United States Patent [19]
Atwood et al.

[11] Patent Number: 5,527,510
[45] Date of Patent: Jun. 18, 1996

[54] IN SITU PCR AMPLIFICATION SYSTEM

[75] Inventors: John G. Atwood, West Redding; Lawrence A. Haff, Wilton, both of Conn.

[73] Assignee: The Perkin-Elmer Corporation, Norwalk, Conn.

[21] Appl. No.: 462,925

[22] Filed: Jun. 5, 1995

Related U.S. Application Data

[62] Division of Ser. No. 261,587, Jun. 17, 1994, which is a division of Ser. No. 17,721, Feb. 16, 1993, Pat. No. 5,364,790.

[51] Int. Cl.$^6$ ............................................. B01L 9/00
[52] U.S. Cl. ..................... 422/104; 422/99; 422/102; 359/391; 359/398; 356/244; 211/41
[58] Field of Search ........................... 422/99, 102, 104; 359/391, 392, 396, 397, 398; 356/244; 211/41

[56] References Cited

U.S. PATENT DOCUMENTS

| | | | |
|---|---|---|---|
| 3,029,695 | 4/1962 | Wolf | 359/398 |
| 3,220,300 | 11/1965 | von Huene | 356/246 |
| 3,233,975 | 2/1966 | McCormick | 435/809 |
| 3,503,665 | 3/1970 | Carter | 435/284 |
| 3,667,088 | 6/1972 | Kurtz | 24/530 |
| 3,879,106 | 4/1975 | McCormick | 359/398 |
| 3,883,398 | 5/1975 | Ono | 435/298 |
| 4,384,193 | 5/1983 | Kledzik et al. | 435/809 |
| 4,683,195 | 7/1987 | Mullis et al. | 435/6 |
| 4,683,202 | 7/1987 | Mullis | 435/91 |
| 4,965,188 | 10/1990 | Mullis et al. | 435/6 |
| 4,974,952 | 12/1990 | Focht | 356/246 |
| 4,985,206 | 1/1991 | Bowman et al. | 422/99 |
| 5,038,852 | 8/1991 | Johnson et al. | 165/12 |
| 5,062,697 | 11/1991 | Mitchell | 359/379 |
| 5,281,516 | 1/1994 | Stapleton et al. | 435/809 |

FOREIGN PATENT DOCUMENTS

| | | |
|---|---|---|
| 0524808A2 | 1/1993 | European Pat. Off. . |
| 9107486 | 5/1991 | WIPO . |
| 9319207 | 9/1993 | WIPO . |

OTHER PUBLICATIONS

Katherine A. Staskus et al, In Situ Amplification Of Visna Virus DNA In Tissue Sections Reveals A Reservoir Of Latently Infected Cells, Microbial Pathogenesis, 11, pp. 67–76 (1991).

Gerard J. Nuovo et al, An Improved Technique For The In Situ Detection Of DNA After Polymerase Chain Reaction Amplification, American Journal of Pathology, vol. 139, No. 6, Dec. 1991, pp. 1239–1244.

Kuo–Ping Chiu et al, Intracellular Amplification Of Proviral DNA In Tissue Sections Using The Polymerase Chain Reaction, The Journal of Histochemistry and Cytochmistry, vol. 40, No. 3, pp. 333–341 (1992).

Paul Komminoth, M. D. et al, In Situ Polymerase Chain Reaction Detection Of Vira DNA, Single–Copy Genes, And Gene Rearrangements In Cell Suspensions And Cytospi Diagnostic Molecular Pathology 1(2): pp. 85–97 (1992).

(List continued on next page.)

*Primary Examiner*—Jill Warden
*Assistant Examiner*—Harold Y. Pyon
*Attorney, Agent, or Firm*—Edwin T. Grimes

[57] ABSTRACT

A complete in situ PCR system for amplification of nucleic acids contained in a prepared cell or tissue sample. The containment system for the PCR sample comprises a glass microscope slide, a specimen sample containing the target nucleic acid sequence mounted on the slide, a flexible plastic cover over the sample, and a retaining assembly fastened to the slide and to the cover to retain and seal a reaction mixture against the sample during thermal cycling. The retaining assembly includes a rigid ring on a rim portion of the cover, a cross beam having spaced parallel rails joined by opposite flat ends, and a pair of clips which are pressed over the ends and opposite sides of the slide to fasten the cross beam and cover to the slide.

5 Claims, 8 Drawing Sheets

OTHER PUBLICATIONS

Ashley T. Haase et al, Amplification And Detection Of Lentiviral DNA Inside Cell Proc. Natl. Acad. Sci. USA 87, pp. 4971–4975 (1990).

Janet Embretson et al, Analysis Of Human Immunodeficiency Virus–Infected Tissues By Amplification And In Situ Hybridization Reveals Latent & Permissive Infection At Single–Cell Resolution Proc. Natl. Acad. Sci. USA 90, pp. 357–361 (1993).

John Findlay, Development Of PCR For In Vitro Diagnostics (1992).

Materials received at the tufts University Symposium on In Situ DNA Hybridization Mar. 1991, entitled "In Situ PCR, General Methods and Applications".

H. J. Wolfe et al, Verh. Dtsch. Ges. Path. 74, pp. 295–300 (1990).

O. Bagasra et al, Detection Of Human Immunodeficiency Virus Type 1 Provirus In Mononuclear Cells By In Situ Polymerase Chain Reaction, New England Journal Of Medicine, 326, #2, pp. 1385–1391 (1992).

Letters to the Editor, Detection Of HIV Provirus By In Situ Polymerase Chain Reaction, New England Journal of Medicine, 327, #21, pp. 1529–1530 (1992).

G. J. Nuovo, Determination Of Human Papillomavirus Type By In Situ Hybridization Analysis: A Comparative Study With Southern Blot Hybridization And Polymerase Chain Reaction, The Journal of Histotechnology, 15, #2, pp. 99–104 (1992).

G. J. Nuovo et al, Detection Of Human Papillomavirus DNA In Formalin–Fixed Tissue By In Situ Hybridization After Amplification By Polymerase Chain Reaction, American Journal of Pathology, 139, #4, pp. 847–854 (1991).

M. J. Embleton et al, In–Cell PCR From MRNA: Amplifying And Linking The Rearranc Immunoglobulin Heavy And Light Chain V–Genes Within Single Cells, Nucleic Acids Research, 20, #15, pp. 3831–3837 (1992).

Diagnostic Molecular Pathology, vol. 1, No. 2, Jun. 1992, New York, US pp. 85–97—Komminoth Et Al. 'In Situ Polymerase Chain Reaction Detection of Viral DNA, Single–Copy Genes, and Gene Rearrangements in Cell Suspensions and Cytospin' p. 86, right column—p. 87, left column.

IN SITU PCR AMPLIFICATION SYSTEM

This is a divisional of copending application(s) Ser. No. 08/261,587 filed on Jun. 17, 1994, which is a divisional of application Ser. No. 08/017,721 filed on Feb. 16, 1993, now U.S. Pat. No. 5,364,790.

BACKGROUND OF THE INVENTION

1. Field of the Invention

This invention generally relates to a system for performing the polymerase chain reaction (PCR) and more particularly to an apparatus and method for performing PCR on a DNA or RNA sample without removing it from its original cell structure.

2. Description of the Related Art

The polymerase chain reaction (PCR) is a process for making a very large number of faithful copies of a segment of double-stranded DNA (amplifying) by thermally cycling one or more molecules of this DNA (the template DNA) in the presence of thermally stable DNA polymerase enzyme, (typically Taq polymerase), the four DNA nucleotide bases and two or more single-stranded DNA primers. These primers are short segments of the order of 20 bases that are complementary to the 5' ends of the two complementary DNA single strands which make up the double-stranded template.

PCR is an immensely valuable technique which is very widely practiced, and has revolutionized the field of molecular biology. The technique is disclosed in detail in U.S. Pat. Nos. 4,683,195, 4,683,202, and 4,965,188. The reaction has until recently been carried out in solution in small reaction vessels, where the DNA to be amplified is in suspension. Apparatus for this process is disclosed in U.S. Pat. No. 5,038,852 and in U.S. patent application No. 07/871,274, filed Apr. 20, 1992.

Recently it has been found possible to apply PCR to amplify specific DNA segments inside cells, without first extracting the DNA from the cells. This technique,is called in situ PCR. The cells may be individual cells, or part of a tissue sample. Most often, in situ PCR is performed on cells or thin slices of tissue mounted on microscope slides. The cells or tissue usually have been fixed by treatment with formalin, or other reagents so that their morphology is preserved and recognizable after treatment.

If the selected DNA segment is amplified in such a way that the amplified product DNA can be selectively stained, then microscopic examination of the PCR treated cells can identify which cells in a tissue sample, if any, contain the specific DNA segment, and even where within the cell it is located. Visualization of the amplified DNA within the cells can be achieved by either of two methods. One method uses a complementary single stranded DNA probe to which a label molecule has been attached. This probe is hybridized to the specific DNA sequences in the amplified sample, if there are any, and the excess probe and label is washed away. Then the locations of the remaining label molecules are rendered visible by treatment with developer reagents. This technique for visualization is called "in situ hybridization", or "indirect detection" of the in situ amplified DNA.

The other method of visualization is to use, during the PCR process, a PCR reagent which includes modified DNA nucleotide bases to which a label molecule has been attached. Many modified bases carrying label molecules will be directly incorporated into the amplified product by the DNA polymerase. The location of the amplified DNA can then be visualized by treating the slide as before with developer reagents. This method is called "direct incorporation detection" of DNA amplified in situ.

The developer reagents in both methods typically include an enzyme such as alkaline phosphatase coupled to a molecule which binds strongly and specifically to the label molecule on the amplified DNA or on the hybridized probe, and a substrate which the enzyme converts into an insoluble, strongly absorbing dye. If the label molecule on the amplified DNA is biotin, then the binding molecule, coupled to the enzyme, is typically avidin. If the label molecule is digoxigenin, then the binding molecule is an anti-digoxigenin antibody. Both kinds of developing reagents have been used in both indirect detection by in situ hybridization and in direct incorporation detection. The labels on the label molecules may be colored, fluorescent, or radioactive.

Both methods of detection of in situ amplified DNA can be very sensitive, detecting from ten to a few hundred copies of the amplified DNA segment in each cell. Both require some post-PCR processing of the slide after the in situ PCR thermal cycling has been completed.

Methods for thermal cycling for in sitU PCR of whole cells differ depending on the cell source. Cells which do not form tissues, such as leukocytes and many cultured cells (such as HeLa cells), do not necessarily require special instrumentation for in situ PCR thermal cycling. Hasse et al, *Proc. Natl. Acad. Sci. USA* 87, 4971–4975 (1990) has reported that suspensions of such fixed cells can be thermal cycled in the same reaction tubes normally employed for solution phase PCR, and the cells subsequently spread on a slide for detection of the amplified product.

Often, however, such cells will be thermally cycled on a slide. They are spread out upon a slide by centrifugation, producing a so-called "cytospin" preparation. Spreading such cells facilitates fixation methods and other pre-PCR sample treatments. This does not require any additional effort, since as cytospin step would be otherwise be required later for visualization of the amplified product upon the slide. Cytospins are amplified identically to tissues mounted on slides.

When cells in tissue sections are to be studied, they must be amplified directly upon a surface, because the thin sections otherwise cannot display the tissue's morphology. The main problems associated with thermal cycling of these tissues are to maintain tissue morphology as well as cell morphology, inhibit evaporation of the PCR reaction mixture over the sample, and to obtain uniform, robustly repeatable results.

To perform in situ PCR on fixed cells or tissue samples on a glass microscope slide, one must first use a slide that has been treated so that the cells or tissue will stick to the slide and not be washed off or floated away by the aqueous reagents of the PCR process, or of the subsequent treatments for visualization of the amplified DNA. Typically a silanized slide, one treated so as to covalently bond 3-aminopropyl triethoxysilane molecules to its surface, works well. Alternatively, coatings of poly (lysine) or gelatin/chrome alum have been used.

Next, the area of the slide with the specimen to be amplified must be covered with an excess of the PCR reagent containing DNA polymerase enzyme, nucleotides, primers and other components at correct concentrations. Then the slide and reagents must be cycled typically 10 to 30 times between temperatures typically near 95° C. and 68° C., but sometimes as low as 37° C., spending at least a fraction of a minute or more at each of two or three selected temperatures during each cycle.

There are several important requirements that must be met during thermal cycling for in situ PCR to be successful. One is that evaporation of water from the reagent must be almost completely prevented. No more than about 5% change from optimum reagent concentrations can be tolerated without lower amplification yields or poorer specificity resulting. Another requirement is that no material hostile to the PCR reaction may be in contact with the reagent during the process. Another is that bubbles of air or dissolved gas which are released by the reagent when it is heated should not disturb the access of the liquid reagent to the entire area to be processed.

Finally, published work on in situ PCR has shown that to preserve highly specific amplification it is often important to assemble the reaction so as to achieve a "hot start" or its chemical equivalent. In a physical hot Start, the complete reagent is neither assembled nor does it come into its first contact with the sample DNA until all the components required for the reaction are at a high temperature. The temperature must be high enough so that not even partial hybridization of the primers can occur at any locations other than the desired template location, in spite of the entire genome of the cell being available for non-specific partial hybridization of the primers. The temperature must also be high enough to prevent primer molecules from joining together to form an amplifiable product called "primer dimer". This safe starting temperature is typically in the range of 68° C. to 75° C., and typically is about 10° C. hotter than the annealing temperature used in the PCR.

One way a "chemical hot start" in a PCR can be achieved is by including, in the reagent, a heat-labile component such as single strand binding protein (SSB) which prevents any extension by the polymerase enzyme until the reaction mixture has been heated in the first PCR cycle to a temperature high enough to prevent non-specific hybridization and also to destroy the heat-labile SSB component. Another way to implement a chemical hot start is to replace the dUTP with Uracil and to add to the reagent the heat-labile enzyme UNG (Uracil-N-Glycosylase) which destroys any PCR products made during a low temperature incubation prior to the first PCR cycle.

A still further way of implementing a chemical hot start is to combine the Taq polymerase enzyme with a Taq antibody before adding it to the reagent. Such a Taq monoclonal antibody has recently been announced by Dr. John Findlay of Kodak Clinical Products Division in a paper entitled "Development of PCR for In Vitro Diagnostics" presented at the 1992 san Diego Conference: Genetic Recognition, held Nov. 18-20, 1992. The Taq antibody binds to the Taq polymerase enzyme and inhibits its function at normal temperatures. However, upon heating the inhibited Taq polymerase to near 95° C., the Taq antibody, a normal protein, is denatured, releasing the Taq polymerase enzyme and allowing it to function normally in the PCR process.

These types of chemical hot starts require inclusion of an often expensive component (e.g. UNG or Taq antibody) in the reagent and may place some undesirable constraints on the performance of the PCR, such as a relatively short time limit after a reagent is prepared before which it must be used, or a lower efficiency of amplification. Therefore, it is usually preferable to perform physical hot starts in in situ PCR if at all feasible.

Workers using in situ PCR today meet the requirements described above in a variety of ways that often they have developed in their own laboratories. The information they obtain using in situ PCR often cannot be obtained in any other way, and it is so valuable that they tolerate extraordinary inconvenience and investment of skill to get it.

A fairly common strategy has been to place a coverslip over a sample to be amplified and to seal it with nail polish or a similar adhesive as taught by Komminoth et al, *Diagnostic Molecular Pathology* 1, #2, 85–97 (1992). It is not unusual for such arrangements to leak, since the nail polish will not adhere strongly to tissue samples. Since all components containing the reagent are rigid, high pressures are produced at the denaturation temperature (typically 94° C.) which can dislodge the nail polish. The hard cover slip can also damage the morphology of the fragile underlying cells if it touches them. This method does not allow for convenient hot starts. Another disadvantage is the requirement for a chloroform treatment of the assembly to dissolve the nail polish after cycling.

Such slides are generally laid upon the sample block of thermal cyclers that have not been explicitly designed for slides. To obtain good thermal contact, Komminoth et al used a spacer between the cycler's sample compartment cover and the slide to press the slide against the sample block. Further, existing thermal cyclers with holes in the thermal block accommodating reaction tubes do not have uniform thermal contact, and therefore, temperature uniformity for slides.

A related technique was demonstrated by Chiu et al, *J. Histochemistry and Cytochemistry* 40, #3, 333–341 (1992) who cultured cells to be studied on chambered slides, and applied in situ PCR to the cells upon the same slide. After culturing, the sample chamber walls were removed, but the gasket between the slide and chambers was left on the slide. In order to run an in-situ PCR, the cells were first covered with a PCR reaction mixture containing hot 2.5% agarose and the slides tightly wrapped with Saran wrap. This method provided a flexible cover for the cells, resting upon the gaskets which avoided injuring the cells. The Saran wrap provided evaporation control. The entire assembly was placed upon a Perkin-Elmer Cetus DNA Thermal Cycler with water added to the long slots between samples. The assembly was covered with plastic film and a plastic lid before cycling.

Nuovo et al, *American Journal of Pathology* 139, #6, 1239–1244 (1992) covered the samples with a coverslip made from flexible, temperature-stable polypropylene. The coverslip was typically anchored over the desired tissue section with a drop of nail polish at one corner. The slide is typically placed in an aluminum "boat" placed upon the sample block of a Perkin-Elmer Cetus DNA Thermal Cycler. This "boat" mainly serves the function to hold the mineral oil that was later added to the slide assembly to prevent evaporation of the reagents. After covering the sample with PCR reaction mixture without Taq DNA polymerase, the temperature of the sample was typically raised to about 65°, and the coverslip partially lifted to allow for the introduction of Taq DNA polymerase into the reaction mixture to initiate the PCR reaction.

The ability to lift up the coverslip allowed a hot start, which was demonstrated to produce major improvements in the specificity and yield of specific PCR product in the in situ PCR amplification. Following enzyme introduction, preheated mineral oil was added to the top and sides of the coverslip. Some of the oil was also drawn under the coverslip by capillary action. Its presence reduced the diameter of the droplet of PCR reagent under the coverslip, and also reduced control over the exact positioning of the droplet of PCR reagent. The method achieves excellent results, but requires one or more highly skilled operators, and is messy and unsuitable for large number of slides.

Another methodology employed to thermal cycle and reduce evaporation and condensation problems is to place slides within plastic bags and thermal cycle them in an air-oven type thermal cycler. For example, Staskus et al, *Microbial Pathogenesis* 1991, 11, 67–76 (1991) and Emberto et al, *Proc. Natl. Acad. Sci. U.S.A.* 90, 357–361 (1993) covered tissues with a coverslip and then mineral oil before placing the slides in a heat sealable plastic pouch cycled in an air-oven thermal cycler. The air oven approach avoids the possible problem of evaporation of water from the sample condensing on the cover slip because the entire assembly is roughly isothermal during thermal cycling.

The major disadvantage to the air oven approach is that poor heat transfer characteristics of the system results in very slow thermal cycling times. Also such systems often exhibit poor temperature uniformity from sample-to-sample in the oven.

In summary, none of the existing methods incorporate all the desirable aspects of good thermal uniformity, evaporation control without mineral oil, small reagent volume, maintenance of cell morphology, the ability to do hot starts, and convenience for assembling large numbers of slides for thermal cycling a position other than horizontal. Almost everyone today uses immersion of the prepared slide in mineral oil to prevent evaporation of water from the reagent during thermal cycling.

The oil overlay is a major inconvenience because usually it must be carefully and completely removed by additional steps after thermal cycling and before subsequent processing with detection reagents. Oil is also sometimes a carrier of contaminants which can kill the PCR.

We have found in experimental work that when containment of the aqueous-based reagent on the sample is achieved by mounting a plastic cover-slip over the specimen and attaching it to the slide by adhesives at the corners or edges, surface tension effects and elution of gas move the liquid reagent about during cycling. As a result, these methods are often not totally reliable. Generally, they require the slide to be horizontal, limiting the ways in which it can be held in a thermal cycler. Efforts to seal the reagent under a cover slip by completely surrounding its perimeter with a sealant adhesive often fail because a gas-tight seal is difficult or impossible to maintain with adhesives alone. In addition, the surface of the slide is usually coated with a thin layer of the specimen under at least part of the perimeter of the cover slip, so there is poor adhesion to the slide.

Accordingly there is a need for a new and improved complete sample containment system for performing in situ PCR. There is a need for a system which provides a convenient physical containment for the reagent physically against the sample which prevents reagent and sample evaporation during thermal cycling. There is also a need for a system which eliminates the need for the use of oil, which uses no adhesives, and does not require the slide to be horizontal during thermal cycling.

SUMMARY OF THE INVENTION

The present invention described below meets the above needs. The containment system in accordance with the present invention comprises a conventional glass slide having mounted thereon a tissue sample containing a target nucleic acid, a flexible cover member over the sample, and a retainer assembly mechanically fastened to the slide for retaining a reagent against the sample on the slide beneath the cover member.

In the system in accordance with the invention, the reagent is contained in contact with the selected portion of the sample specimen by a thin, compliant cover which is clamped mechanically to the slide. This cover may be opaque or transparent as the reagent will preferably be viewed through the glass during assembly rather than through the cover, and must be inert to the PCR reagents and sample. A generally circular seal ring around the perimeter of the cover presses the cover against the slide to maintain the hermetic seal. Pressure is maintained by a spring clip and cross beam arrangement. The amplified sample on the slide will be viewed in a conventional manner through a microscope after the cover and its retainer have been removed.

The system makes assembly of the complete reaction on the slide quick, convenient and repeatable and requires minimal skill. The assembly procedure is easily compatible with physical hot starts. Finally, the system of the invention is compatible with conventional microscopic detection techniques.

These and other features, objects and advantages of the invention will become more apparent from a reading of the following detailed description when taken in conjunction with the accompanying drawing.

DETAILED DESCRIPTION OF THE INVENTION

Figure 1:
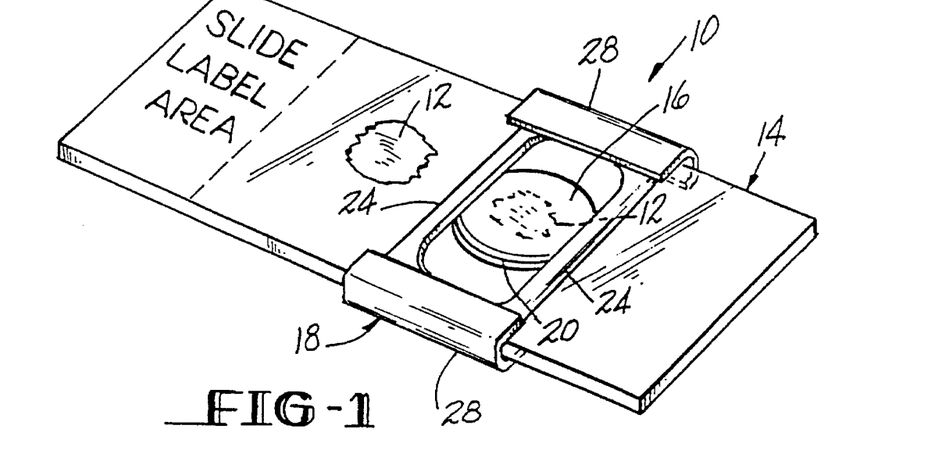
FIG. 1 is a perspective view of a sample containment system assembly in accordance with the invention.

The containment system 10, for retaining a sample specimen 12 containing a target nucleic acid and a reagent 13 on the sample 12 mounted on a glass slide 14, in accordance with the invention, is shown in FIG. 1. The system 10 comprises the glass slide 14, a generally compliant cover member 16 over the sample 12, and a retaining assembly 18 fastening the cover 16 to the slide 14.

Figure 2:
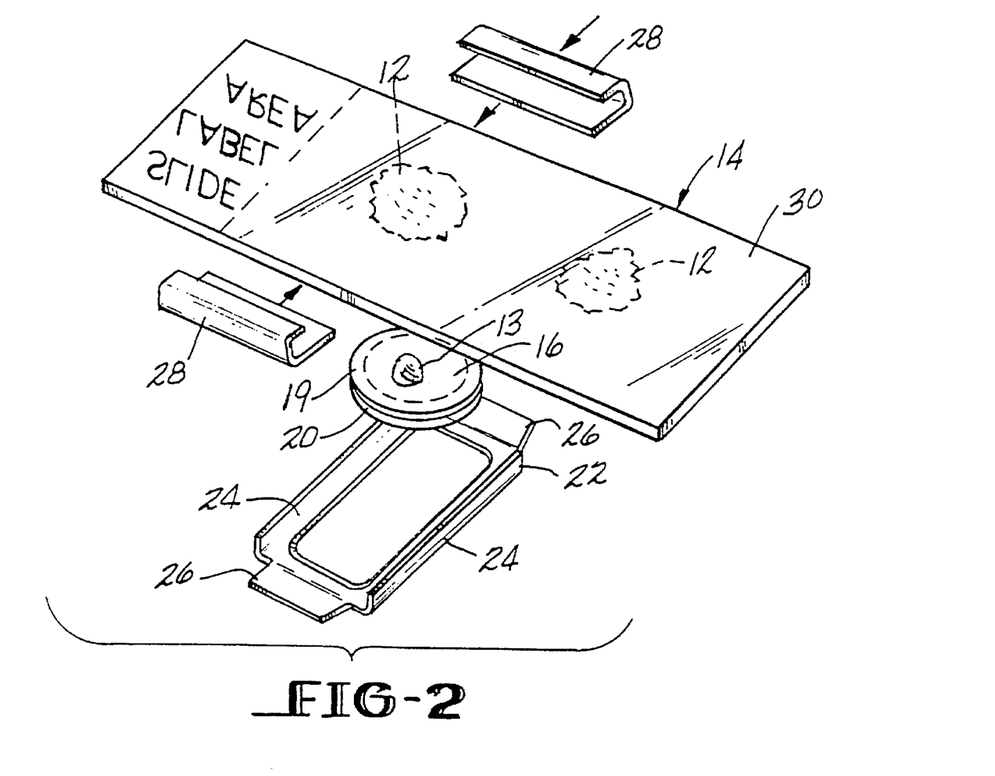
FIG. 2 is an exploded view of the system assembly shown in FIG. 1, shown upside down, the way it is assembled.
Figure 3:
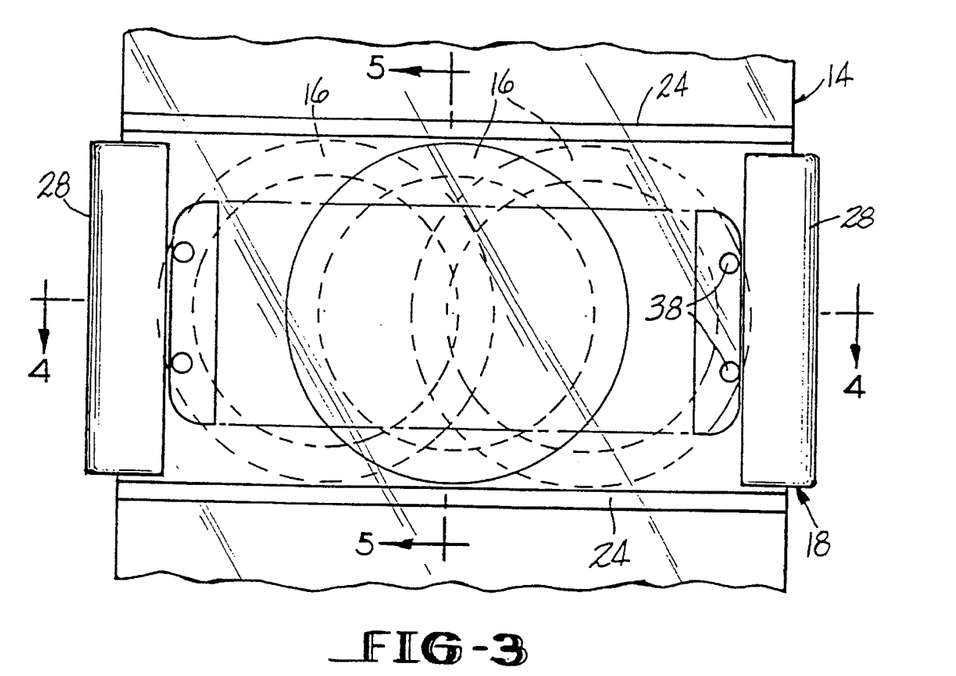
FIG. 3 is an enlarged partial top view of the assembly shown in FIG. 1, shown upside down.
Figure 4:
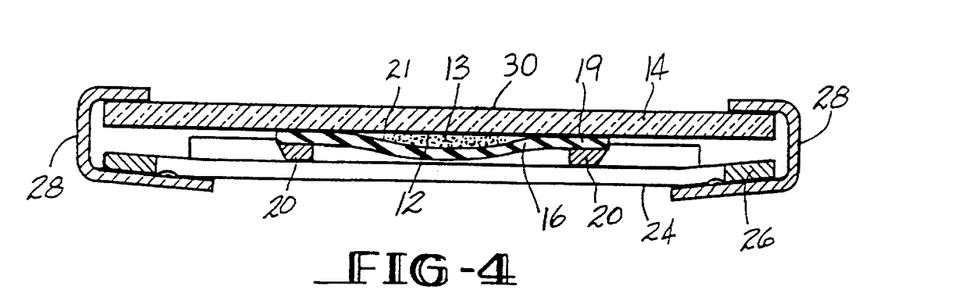
FIG. 4 is a sectional view of the assembly taken along the line 4—4 in FIG. 3.
Figure 5:
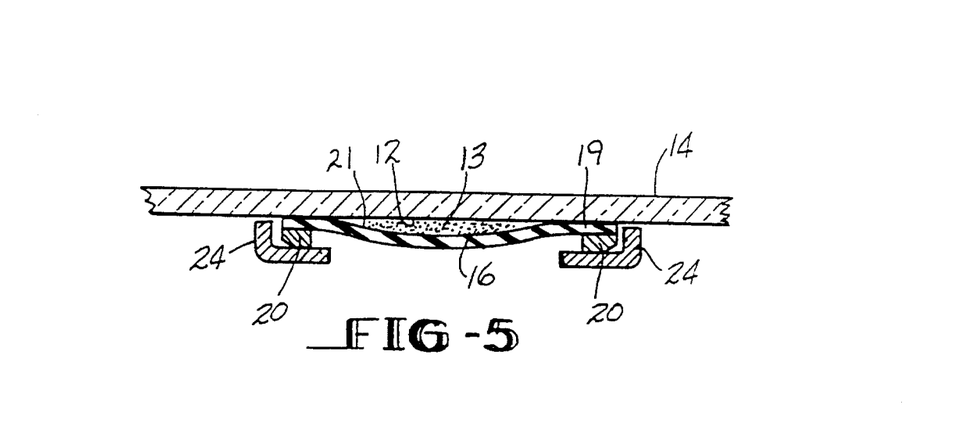
FIG. 5 is a cross sectional view of the assembly taken along the line 5—5 in FIG. 3.

This system assembly 10 is shown in perspective in FIG. 1. FIG. 2 shows an exploded view of the individual parts, and FIG. 3 shows an enlarged top view of the assembled system shown in FIG. 1. FIGS. 4 and 5 show cross-sections of the system 10 shown in FIG. 3.

The reagent 13, about one drop, is sealed into the volume between the cover member 16 and the slide 14 by a compliant seal member or gasket around its perimeter. The seal member may be a separate piece or may be an integral part of the cover 16. The seal is preferably the compliant rim portion 19 of the cover member 16 which is made of an elastomer which is chemically compatible with the PCR reagents. In the preferred embodiment, it is made of silicone rubber. It is wide enough, and compressed with sufficient force per unit area by a rigid seal ring 20 against the slide 14 so that even when the slide's surface under the seal ring is covered with a thin layer of cells or tissue of the sample 12, very little water, liquid or vapor, can escape from the space beneath the cover 16 during thermal cycling. The gasket seal is still maintained even at boiling temperature conditions.

The compliant cover 16 is shaped so that, when relaxed, it is gently concave on the side touching the reagent. The degree of concavity is chosen to define the volume of reagent 13 that will be contained between the cover 16 and the slide when the seal ring 20 presses the rim portion 19 of the cover 16 against the slide 14. Typically, for a circular cover about 12 mm in diameter, this is about 10 microliters. The volume is chosen as follows. If the volume is too large, the amount of reagent 13 required will be unnecessarily expensive, and will take a little longer to heat and cool. If it is too small, the surface to volume ratio under the cover will become unfavorably large, with greater risk of poor amplification due to adsorption of enzyme on the surfaces, or poisoning of the reagent 13 by traces of inhibitory contaminants on the parts or on the specimen 12.

Typically the interesting area of the sample 12 to be examined is no larger than 10 mm in diameter. The clear area of the slide is about 25 mm by 57 mm since one end is usually frosted for labeling. Since it is quite difficult to deposit a tissue section only a few microns thick precisely at a pre-selected location on the slide, it is desirable to make the cover 16 capable of being located anywhere in the clear area. Also, there may be more than one interesting area on a slide, so it is an advantage to be able to mount more than one sample and system 10 on a slide, as shown in FIG. 1.

The new retaining assembly 18 for clamping the cover 16 to the slide 14 permits a widely variable location for the cover 16. Samples located anywhere within a margin of a few millimeters of the edges of the clear area of the slide can be contained and amplified. The few millimeters margin is needed for the seal ring 20. The rim portion 19 of the cover 16 is reinforced by the rigid seal ring 20 around its perimeter such that if the seal ring 20 at two opposite edges of the cover is compressed against the slide 14 to make an adequate seal, then the seal will be adequate at all other parts of the perimeter of the cover. The rigid seal ring 20 thus constrains the perimeter of the cover to remain in one plane.

The cover 16 is preferably a circular disk of thin rubber sheet. The rigid seal ring 20 is a stainless steel ring bonded to the rim 19 of the rubber cover 16. The ring 20 may have a rectangular, trapezoidal, triangular or other polygonal cross sectional shape so there is at least one flat side for bonding with the cover 16. Most preferably, the ring 20 has a rectangular or trapezoidal cross sectional shape. A "D" shape cross section would also be permissible. In addition, the ring need not be round. It may be oblong or other continuous shape so long as the cover 16 can be sealed to the slide surface. The rim 19 of the rubber disk cover 16 which is bonded to the steel ring 20 thus forms a gasket which is continuous with the rest of the disk. This embodiment requires that the thin rubber sheet cover 16 be impervious to the diffusion of water vapor through it and at the same time not hostile to the PCR reagents. Silicone rubber, though not hostile to PCR, is too permeable to water vapor. Accordingly, either a sandwich or composite of a non-hostile elastomer such as silicone rubber and a non-permeable elastomer such as polypropylene, or a non-hostile coating or layer 21 such as Parylene C from Union Carbide on at least the underside of a non-permeable elastomer layer may be preferable as a cover material as indicated in FIGS. 4 and 5.

The necessary concave shape of the cover 16 can be achieved during molding or by deforming the flat sheet cover 16 while it is being bonded to the rigid ring 20, or by attaching the center of the outside surface of the cover 16 to a cross-piece attached to the ring 20 (not shown) to hold the center of the disk slightly out of the plane of the ring 20.

The cover 16 is held against the slide 14 by a rigid cross beam 22 with parallel rails 24 which touch only opposite portions of the seal ring 20. The rails 24 of the beam 22 extend across the slide from one long edge to the other. Thus the cover 16 can be located anywhere on the cross beam 22, as shown in FIG. 3. Also, the cross beam 22 can be clamped to the slide anywhere along the slide's length. Therefore, in the present invention, the cover 16 can be placed anywhere within the clear area of the slide.

The rails 24 of the cross beam 22 preferably have an L-shaped cross section as shown in FIG. 5 to enhance rigidity. The rails 24 are joined by flat ends 26 which are clamped to the slide 14 by two clips 28 as shown in FIGS. 1, 3, and 4. These clips 28 each extend over the long edges to the back side 30 of the slide 14, the side opposite to that carrying the sample 12. Each end 26 of the cross beam 22 is slightly bent to form an inclined plane. As the clips 28 are pushed into place, they slide on these inclined plane ends 26 and apply substantial compressive force on the cross beam 22 and the seal ring 20 to compress the rim portion 19 of the cover 16 and against the slide 14.

Although the clips 28 and the cross beam 22 may be made of relatively thin material, probably stainless steel, they are sufficiently rigid so that, during the assembly, they flex very little. The stored energy that sustains the clamping force preferably comes largely from compression of the rubber gasket (the rim 19 of the cover 16 beneath the seal ring 20), not from flexure of the cross beam 22 or clips 28. The beneficial consequence of this is that no matter where the cover 16 is located on the slide 14, the rails 24 of the cross beam 22 are always parallel to the slide and the rim 19 is compressed the same amount, uniformly around its entire perimeter. The cross beam 22 and clips 28 clamping the cover 16 to the slide 14 are also sufficiently rigid to resist the pressure increase caused by heating the reagent 13 to nearly boiling temperature. The fact that the cover 16 is compliant greatly reduces the maximum pressure that can occur beneath the cover. In addition, the compliant cover 16 resists fluidic expansion during heating without breaking the slide 14 which effectively pressurizes the enclosed volume. This may prevent or at least minimize bubble formation in this reagent 13 during thermal cycling, making use of the containment system of the invention altitude independent. The compressive force applied to the ring by the cross beam is in the range of four pounds force and results in about 20% compression of the rubber rim 19.

Figure 6:
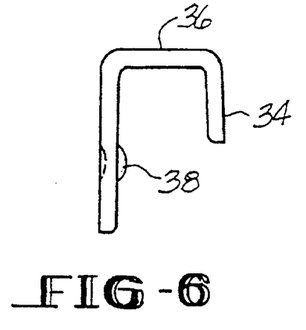
FIG. 6 is an end view of one of the spring clips in accordance with the invention.
Figure 7:
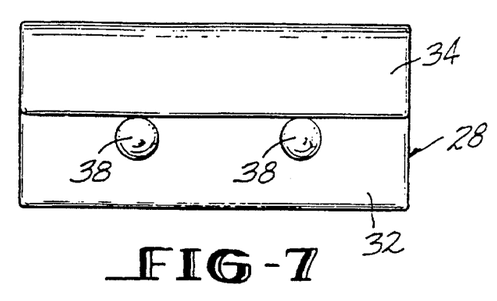
FIG. 7 is a top view of the spring clip shown in FIG. 6.

Enlarged top and end views of one of the clips 28 are shown in FIGS. 6 and 7. The clip 28 is a piece of stainless steel sheet metal bent into a "J" shape to form a long side 32, and a short side 34, and a connecting perpendicular side 36. Side 32 may have a pair of dimples 38 protruding toward short side 34. These dimples 38 are spaced so as to engage and snap over and engage the inside edge of the inclined plane end 26 of the cross beam 22 to latch the clip 28, the cross beam 22, and slide 14 together as shown in FIGS. 1 and 4. Alternatively, the function of the dimples 38 may be performed by a raised ridge or other interference mechanism between the mating retaining assembly 18 parts.

Figure 8:
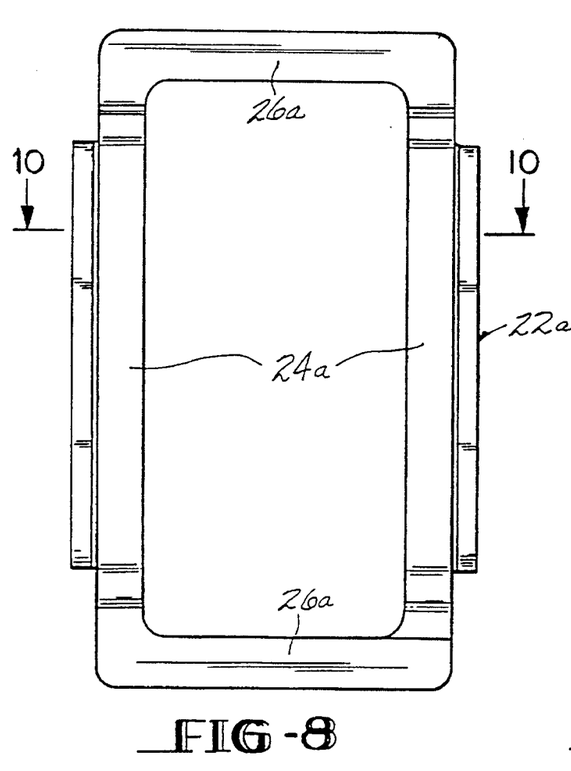
FIG. 8 is a bottom view of a preferred cross beam used in the assembly in accordance with the invention.
Figure 9:
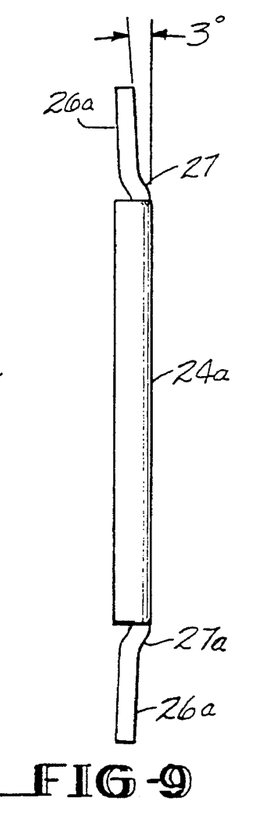
FIG. 9 is a side view of the cross beam shown in FIG. 8.
Figure 10:
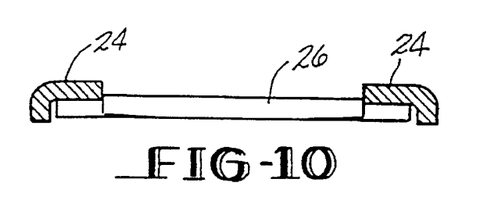
FIG. 10 is a cross sectional view of the cross beam in FIG. 8 taken along the line 10—10.

An alternative preferred embodiment of the cross beam 22 is shown in FIGS. 8, 9, and 10. The cross beam 22a is generally a stamped rectangular sheet metal body with a rectangular opening forming two parallel rails 24a joined by transverse ends 26a. The rails 24a of the cross beam 22a have an L-shaped cross section as shown in FIG. 10. Upon assembly, the rails 24a, joined by flat ends 26a, are clamped to the slide 14 as above described. The principal difference from the first cross beam 22 shown in FIGS. 3 through 5 is that ends 26a join with rails 24a in a double bend 27a. The double bend 27a permits the long leg of the clip 28 to frictionally engage with the surface of end 26a. This double bend 27a also creates almost a step so that the overall thickness of the assembled slide and cover assembly is minimized when the clip 28 is installed.

An approximately 3° slope to the ends 26a is sufficient to provide the necessary gripping force between the beam ends 26a, slide 14, and clip 28, and ensure a sufficient pressure on the rigid ring 20. Thus, when this alternative beam shown in FIGS. 8–10 is used, the dimples 38 on the clips 28 are not necessary.

Since the cover 16 is no larger than necessary, the volume of reagent required is no more than necessary, and the force necessary to make a leak-tight seal with the seal ring is also minimized. All of these attributes are advantageous. It is desirable to not need great sealing force because it makes assembly easier, and the mechanism necessary to rigidly sustain a larger force would make the assembly unnecessarily thick and massive. This, in turn will limit the number of slides which can be accommodated simultaneously in a cycler if they are mounted on edge. It would also increase the thermal time-constant of the assembly, and slow the cycling process.

Assembly of a Slide for In Situ PCR

Figure 11:
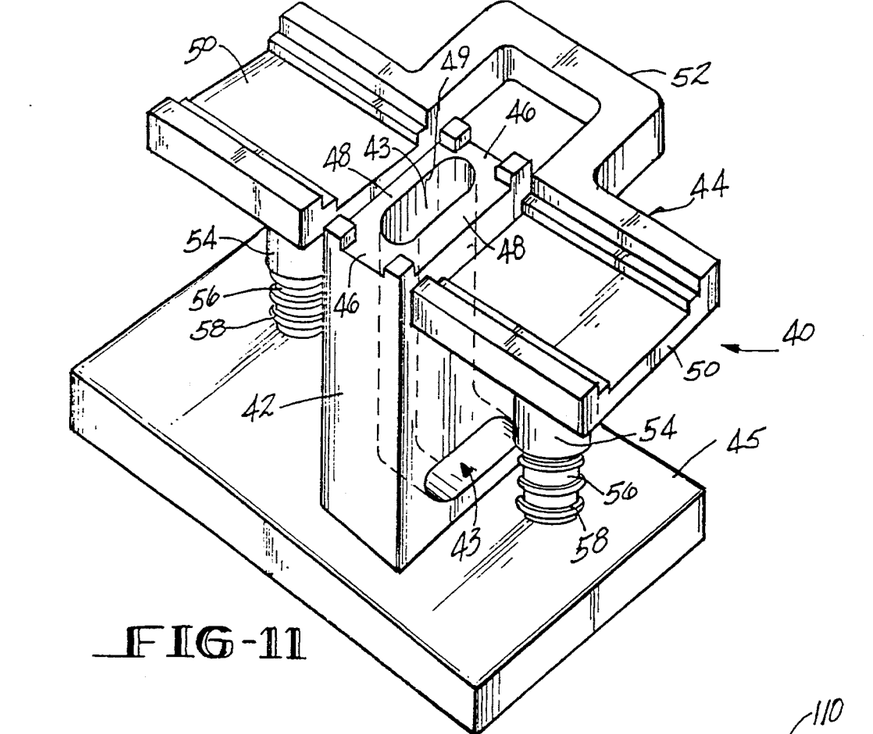
FIG. 11 is a perspective view of a manual assembly fixture for the containment system of the invention.
Figure 12:
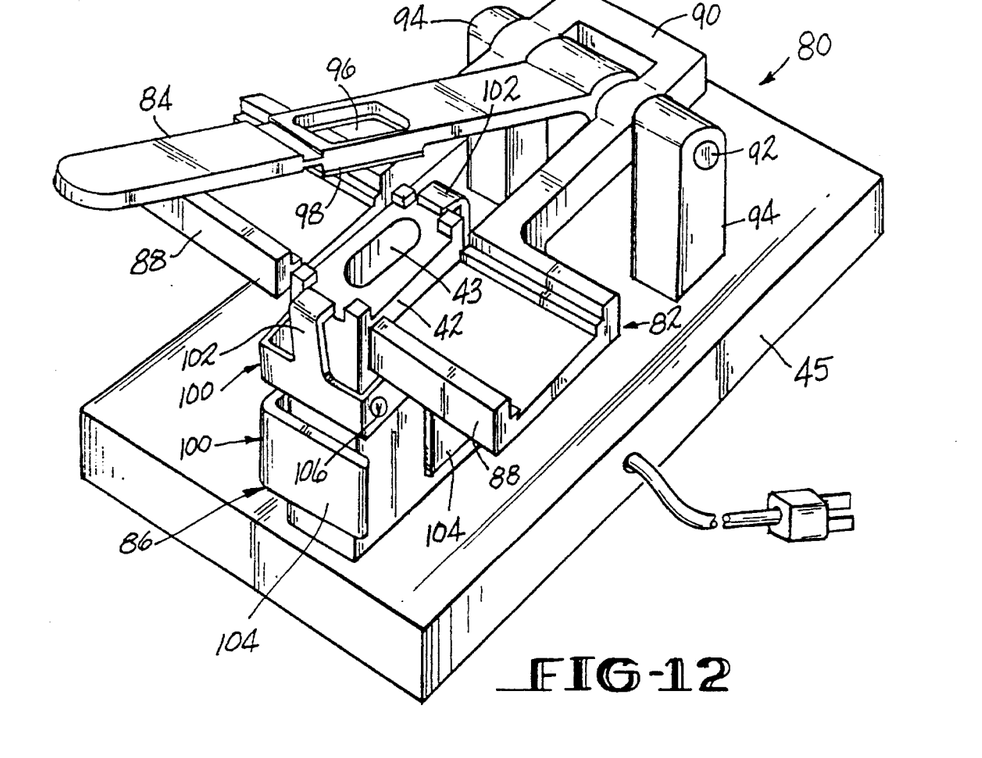
FIG. 12 is a perspective view of a mechanical assembly apparatus for the containment system in accordance with the present invention.

Assembly of the complete containment system 10 on a slide 14 with reagent 13 in place under the cover 16 is accomplished by a unique procedure which is also part of the present invention. In one preferred embodiment, a manual assembly fixture 40 is used. This fixture 40 is shown in FIG. 11. In another preferred embodiment, a mechanically assisted assembly fixture or tool is used. Such a tool is shown in FIG. 12.

The manual assembly fixture 40 shown in FIG. 11 basically consists of an assembly post 42 fixed to a base 45 and a slide guide 44 movably mounted on the base 45. The slide guide 44 is spring biased upward so as to move vertically around the post 42. The top of the post 42 has recessed areas 46 and 48 that are shaped to loosely receive the clips 28 and the cross beam 22 to hold them in position for assembly to the slide 14. The post 42 also has a central air passage 43.

The slide guide 44 is a U-shaped body which has two generally flat tray portions 50 positioned adjacent opposite sides of the post 42. These tray portions 50 have a channel sized to receive a standard microscope slide. The two tray portions 50 are connected together by an integral U-shaped yoke 52. Each tray portion 50 has a sleeve 54 fixed to its underside which slides over a mating pin 56 fixed to the base 45. Springs 58 mounted around the pins 56 bias the guide upward to a position in which a slide 14 held by the tray portions 44 will be positioned above the recessed areas 46 and 48 in the top of the post 42.

Assembly of the containment system 10 is as follows. First the two clips 28 are placed in recessed areas 46 on top of the assembly post 42 with their long sides 32 down against the post 42. They are then positioned so that the space between their facing short sides 34 is just a little wider than the width of a standard 1 inch microscope slide. Next, the cross beam 22 is placed on the assembly post in between the depressions 46 with its rail edges upward as in FIG. 2 and the rails 24 in the recessed areas 48. The dimensions of the various parts are such that a portion of each of the inclined planes formed by the ends 26 of the cross beam 22 lie on top of the long sides 32 of the clips 28. Thus, the initial engagement of the clips 28 with the cross beam 22 is first established.

Alternatively, a pre-assembled combination of the cross beam 22 and two clips 28, held in the initially engaged and appropriately spaced relationship by a weak adhesive, can be provided to reduce the amount of manipulation necessary to prepare the assembly 18. In addition, if the clips 28 are made of magnetic stainless steel, then small permanent magnets, embedded in the assembly post, could automatically position the clips properly with minimal manipulation.

Next, the cover 16, with seal ring 20 attached to the rim portion 19, is placed on and between the rails 24 of the cross beam 22 with the concave, gasket side of the cover 16 up and the seal ring 20 resting on the rails 24 of the cross beam 22.

The cover 16 is then positioned such that it is centered under the area of interest (containing the sample) on the slide 14. The cover's dimensions are such that its rim 19, i.e. the gasket or seal surface, projects above the rails of the cross beam 22 by more than the amount that the gasket will be compressed when assembled, so that even after the rim 19 is compressed, the cross beam 22 will preferably not actually touch the glass slide 14, as is shown in FIGS. 4 and 5.

A droplet of reagent 13 is then placed on the cover 16. A piper set to deliver the desired reagent volume is preferably used, by hand, to deliver the reagent as a droplet close to the center of the concave surface. Since the cover's surface is only partially wettable, the droplet does not spread significantly. It also stands up well above the rim 19 of the cover 16.

The slide 14, having at least one specimen sample 12 previously fixed thereto, is then placed on the slide guide 44 of the assembly fixture 40 with the sample side down, directly over the droplet of reagent 13. The slide guide 44 is initially positioned so that the bottom of the slide is always held at least a few millimeters above the top of the reagent droplet 13 by springs 58. The slide 14 is positioned by sliding it in its long direction so as to center the sample area to be processed over the droplet on the cover 16. This can be done by looking through the back of the slide 14 (which is now on top). It is made especially easy if, as is common practice, the area of interest is circled with a china-marker on the back 30 of the slide 14.

Next, the user places a finger (gloved) on the back 30 of the slide 14 directly over the assembly post 42 and presses directly down with enough force to overcome the upward-pushing springs 58 and move the slide guide 44 down. This causes the sample side of the slide 14 to make contact with the reagent droplet 13 and forces the droplet 13 to spread out over the slide 14 and the cover surface within the rim 19. The volume of the reagent droplet has been chosen to be slightly larger than the volume between the concave surface of the cover 16 and a plane touching its rim 19 (the slide surface). Therefore the droplet 13 reaches and passes over the edge of the rim 19 just before the slide surface makes contact with the rim 19. This expels all, or very nearly all, of the air from under the cover 16 before the slide 14 and cover rim 19 form a seal. It is acceptable for a small excess volume of the reagent to spill out past the rim 19 of the cover 16. It will eventually dry up. Further downward force on the slide 14 starts to compress the rim 19.

When the rim 19 has been partially compressed, the back side 30 of the slide 14 should be just at or below the bottom edge of the short side 34 of each of the clips 28. At this point, the operator uses the (gloved) thumb and finger of his other hand to squeeze the two clips 28 toward each other, over the edges of the slide 14, and over the ends 26 of the cross beam 22, until the clips 28 stop with their vertical connecting sides 36 against the edges of the slide 14. This action completes the compression of the rim 19 of the cover 16. The clips 28 stay in place until intentionally removed because of the small detents 38 that engage the ends 26 of the cross beam 22, and/or because the tangent of the angle of the inclined plane on each of the cross beam ends 26 is smaller than the coefficient of friction between the clip 28 and the cross beam end 26.

In the assembled system 10 in accordance with the invention, the volume trapped between the slide 14 and the cover 16 is entirely filled with incompressible reagent liquid 13. Thus, as the rim portion 19 of the cover 16 is compressed to completion, it is preferable for the cover itself to be compliant, so that it can expand to accommodate the fixed reagent volume without a large increase in pressure, which otherwise would make assembly difficult. Another reason why the cover 16 should be compliant is that when the reagent 13 is heated to a temperature approaching or beyond its boiling point, it expands, its vapor pressure rises, and gases dissolved in it tend to come out of solution. If the cover were not at all compliant, the pressure within it might rise enough to break the slide or the cover seal and cause loss of reagent. But a small amount of compliance, enough to accommodate the volume of any gas bubbles that form, keeps the pressure from rising too much. It generally will rise to only a little more than the excess of the reagent vapor pressure over external atmospheric pressure. This will assure that the system will work well, even at high altitudes at which the boiling point of the free reagent becomes lower than the PCR denaturation temperature.

A mechanically assisted assembly apparatus or tool 80 is shown in FIG. 12. This tool is similar to the tool shown in FIG. 11 except that handling the assembly with fingers is virtually eliminated. This tool 80 is preferred, especially if physical hot starts (described in detail below) are to be implemented. The tool 80 shown in FIG. 12 has a base 45 and a post 42 mounted thereon as in FIG. 11 and utilizes a slide guide 82 somewhat similar in shape to the guide 44 shown in FIG. 11. In addition, tool 80 has a compression arm 84 and a clip installation mechanism 86 so that the user does not have to physically touch a hot component of a retaining assembly 18 during the assembly operation.

The slide guide 82 has a pair of spaced flat tray portions 88 sized to receive a slide 14. The tray portions are joined by an integral, U-shaped yoke 90, which rotates about a horizontal pivot pin 92. Pivot pin 92 is horizontally supported above the base 45 by two fixed supports 94 at about the same height as the top of the post 42.

One end of the compression arm 84 is also pivotally mounted inside the yoke 90 on pin 92. Arm 84 is a flat, elongated member with a generally rectangular opening 96 positioned over the top of the post 42 which receives and supports the cross beam 22 and clips 28. The opening 96 permits observation of the cover member 16, cross beam 22, and sample 12 on the slide 14 as the arm 84 is lowered over post 42 onto the slide 14. A rubber cushion pad 98 encircling opening 96 is used to preclude slide breakage when the arm 94 is pressed against the slide 14. The arm 94 is preferably spring biased upward to keep it raised out of the way until needed. Similarly, the slide guide 82 is spring biased upward to keep the slide 14 above the cross beam 22, clips 28, cover member 16, and reagent drop 13 until the arm 94 is lowered for final installation of the retaining assembly 18 to the slide 14. Both the arm 84 and the slide guide 82 may have conventional springs (not shown) mounted on pin 90 or the springs may extend from the base 45 to provide the desired upward bias.

The clip installation mechanism 86 is preferably a pair of spring loaded pliers 100 mounted on the post 42 having two opposing fingers 102 each bent toward a recessed area 46 which positions a clip 28 adjacent the edge of the slide 14 mounted in the guide 82, and an integral opposing handle portions 104. The opposing handle portions 104 of the pliers 100 are manually squeezed together to push the clips 28 onto the sides of the slide over the slide edges and the ends 26 of the cross beam 22 to complete assembly of the containment system 10. Each plier 100 is pivotally mounted on a stationary pivot pin 106 which projects through the side of the post 42, directly under the point of contact between the fingers 102 and clips 28.

Figure 13:
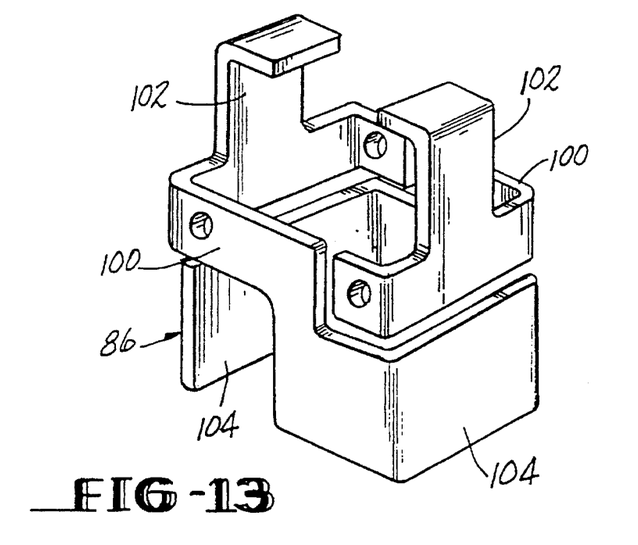
FIG. 13 is a perspective view of the plier assembly separated from the apparatus of FIG. 12.

The clip installation mechanism 84 is shown separately in perspective in FIG. 13. Each L-shaped finger 102 has a short leg which fits into one of the recessed areas 46 in the top of the post 42. Each flat handle portion 104 wraps around two adjacent sides of the post 42. A spring (not shown) positioned between each handle portion 104 and the post 42 (not shown) biases the handle portions 104 and finger portions 102 of the pliers 100 outward to permit installation of the retaining clips 28 in the recesses 46. When the opposing handle portions 104 are squeezed together, the tips 102 move toward each other, forcing the clips 28 onto the slide 14.

The tool 80 is operated as follows. Two clips 28 are installed in the recesses 46 as previously described. The cross member 22, seal ring 20, cover 16, and reagent 13 are placed sequentially on the post 42 and A slide 14 with a sample 12 mounted thereto is then placed in the tray portion 86 of the guide 82 with the sample side down and the sample positioned vertically above the reagent 13 in the cover 16. The compression arm 94 is then pivoted downward against the slide to lower the slide 14 onto the cover 16 and spread the reagent and enzyme over the sample on the slide 14. When the arm 94 is fully lowered, the pliers 100 are squeezed, moving the fingers 102 toward each other, pushing the retaining clips 28 onto the slide 14 and cross beam ends 26. The complete slide assembly 10 is then removed from the tool 80, placed in a modified thermal cycler, and thermally cycled as above described.

Hot Start Applications

To implement hot starts using this invention, we require only to add a heating system to the manual assembly fixture 40 or mechanically assisted tool 80, and use heated containers to store the components of the system. Also, as above described, some of the slide and retaining assembly components may be temporarily assembled together and heated prior to placement on the fixture and final joinder of all containment system components.

The following description applies to the manual heated assembly fixture 40 is shown in FIG. 11 and analogously to the mechanically assisted assembly tool 80 shown in FIG. 12. The assembly post 42 is made with a vertical bore or air passage 43 through it which at the bottom communicates with ambient air. An internal thermostatically controlled heater, when turned on, keeps the body of the post 42 at about 75° C., which is hotter than the hot start temperature, approximately 70° C. This heater may be a resistance coil wrapped around the central bore 43 or may simply be embedded in the base 45 or in the post 42. Fins on the interior of the bore 43 may be provided to help heat the air rising in the vertical passage. Convection maintains a rising column of hot air, as in a chimney, which bathes the cross beam 22 and cover 16 mounted on the top of the post 42 prior to final assembly. The cross beam 22 and clips 28 are also heated by contact with the metal assembly post 42.

The slides 14 to be processed are stored in a heated carrier that maintains them at about 75° C. The clips 28, covers 16, and cross beams 22 can be stored in small heated containers at the work station, and handled with tweezers. The time required to mount two pre-heated clips, a cross beam and a cover onto the heated assembly post 42 might typically be 10 to 15 seconds. The time to transfer pre-heated reagent 13, using a pre-heated positive displacement pipette tip, is less than 10 seconds. The heated reagent 13 needs to be exposed no more than another 10 seconds before the pre-heated slide is pushed down to seal it and fasten the components of the retention assembly 18 together. A few seconds later the assembled slide can be back in its heated carrier, never having been cooler than 70° C. Concentration of the reagent by evaporation should thus be minimal because the exposure time is so short.

A true physical hot start is achievable merely by heating the assembly tool and storing the slides, containment parts, reagent, and pipette tips in heated carriers at the assembly work station. No other change in procedure is necessary. This procedure is simplified with the use of the assembly tool 80 shown in FIG. 12 since the storage of heated components and contact with the heated components and guide 82 is obviated. Pre-assemblies of clips 28 and cross beams 22 could also be used for hot starts if the components are attached together by an adhesive that is strong at ambient temperatures, facilitating packaging and shipment, but weakens at the hot start temperature for easy, final assembly.

Thermal Cycling the Assembly

The clips 28 of the containment system 10 overhang the edges of the slide 14 and occupy a few millimeters of its back side 30. Because of this, the flat heat exchanging surface of any thermal cycler which is used with the new containment system must be provided with grooves which are slightly less than 1 mm deep and 3 mm wide to accommodate the clips 28.

Figures 14, 15:
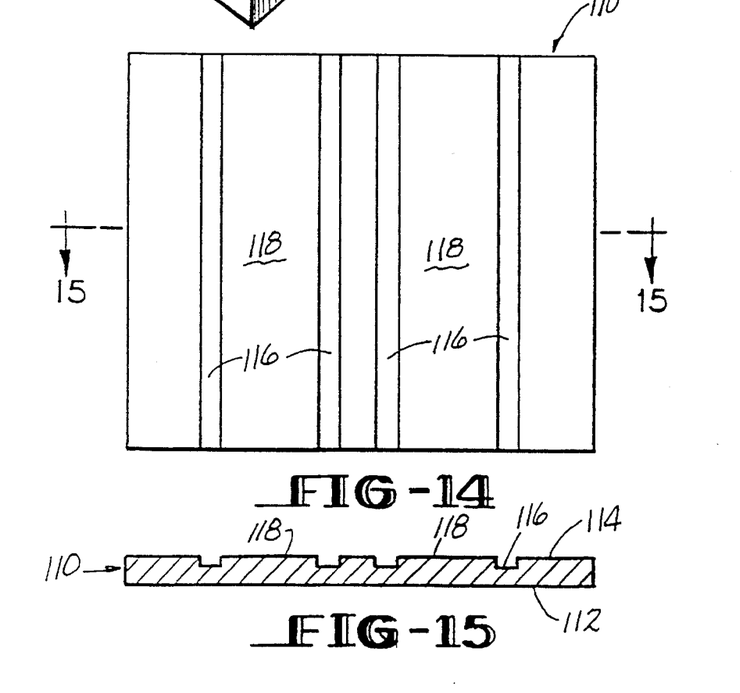
FIG. 14 is a top view of a grooved adapter plate for an existing thermal cycler.
FIG. 15 is a sectional view of the grooved adapter plate shown in FIG. 14.

An existing thermal cycler such as the Perkin Elmer DNA Thermal Cycler, the Perkin Elmer Model 480, or the Perkin Elmer Model 9600 may be utilized to thermally cycle slide assemblies in accordance with the present invention if an adapter plate is placed on the flat upper surface of the thermal cycler block. Such an adapter plate 110 is shown in top and sectional views in FIGS. 14 and 15. This plate 110 has a flat bottom surface 112 and top surface 114 which has spaced parallel grooves 116. These grooves 116 are sized to receive clips 28 so that the flat surface portion 118 between the grooves 116 fully contacts the glass surface of the slide 14 placed on the adapter plate. The adapter plate 110 may be designed to accommodate up to 3 or 4 slide assemblies.

A heat conductive liquid such as an oil or thermally conductive grease is preferably spread on the upper surface portion 118 to increase the thermal contact across the interface between the back side 30 of the slide 14 and the flat heat exchange surface 118 between the grooves 116. A silicone grease or mineral oil should also be used between the thermal cycler block and the adapter plate 110 to ensure good thermal contact across this interface. Ethylene glycol or its polymers can also be used advantageously to provide the good thermal contact between both interfaces. Ethylene glycol or its polymers have the advantage of being water soluble, thus simplifying the cleansing of assembly components and the thermal cycler block. Another advantage of using either oil, grease, or ethylene glycol or its polymers between the slides and the adapter plate and between the thermal cycler block and the adapter plate is that the liquid layer acts as a suction clamp to retain the slides to the adapter plate and the adapter plate in place on the block, thus minimizing the chance of droppage during handling.

Present experiments have shown that it may be necessary to readjust the thermal calibration of the DNA Thermal Cycler, or specify slightly higher temperatures for in situ amplifications to compensate for the changes in thermal mass of the whole system. For example, a small drop in temperature of up to 1° C. from the sample block to the top of the slide surface has been observed. This drop in temperature is minimized by the use of oil, grease, or ethylene glycol as mentioned above.

An In Situ Version of the DNA Thermal Cycler

Figure 16:
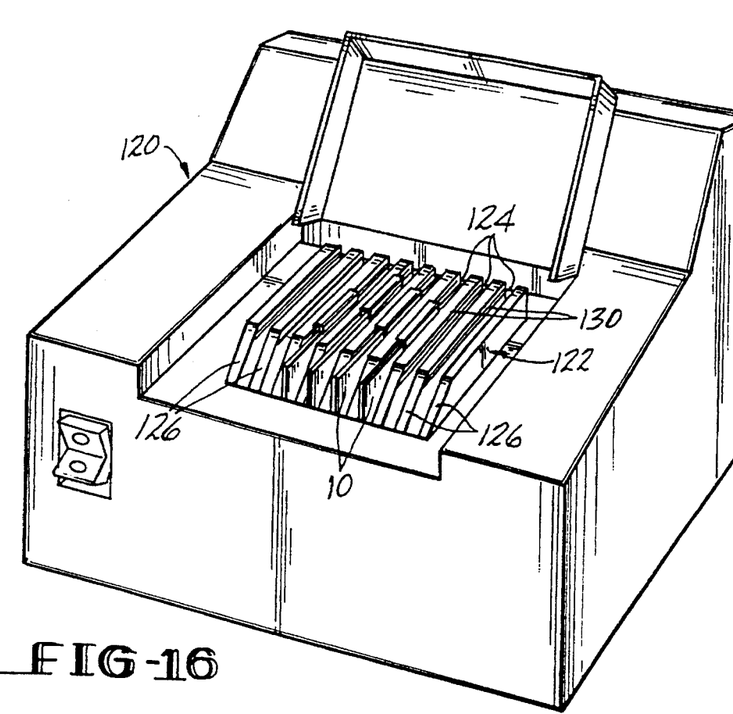
FIG. 16 is a perspective view of a thermal cycler having a modified heat exchanger block adapted to receive the sample containment systems in accordance with the present invention.

The containment system 10 of the invention is adaptable for cycling larger numbers of slides than just discussed because each assembly 10 is less than 4 mm thick, may be cycled in any physical position, and does not require submersion in oil. For example, the assemblies 10 may be vertically arranged in a modified thermal cycler block to accommodate a greater number of slide assemblies. A modified thermal cycler 120 containing a modified metal block 122 is shown in FIG. 16. The block 122 contains 8 slots 124 which are 10 mm apart on centers between metal partitions 126 therebetween. Each slot 124 is about 5 mm wide and each partition 126 has a flat vertical heat exchange surface 128 with the necessary pair of grooves 130 for receiving the clips 28 on the right hand side of each metal partition 126.

Figure 17:
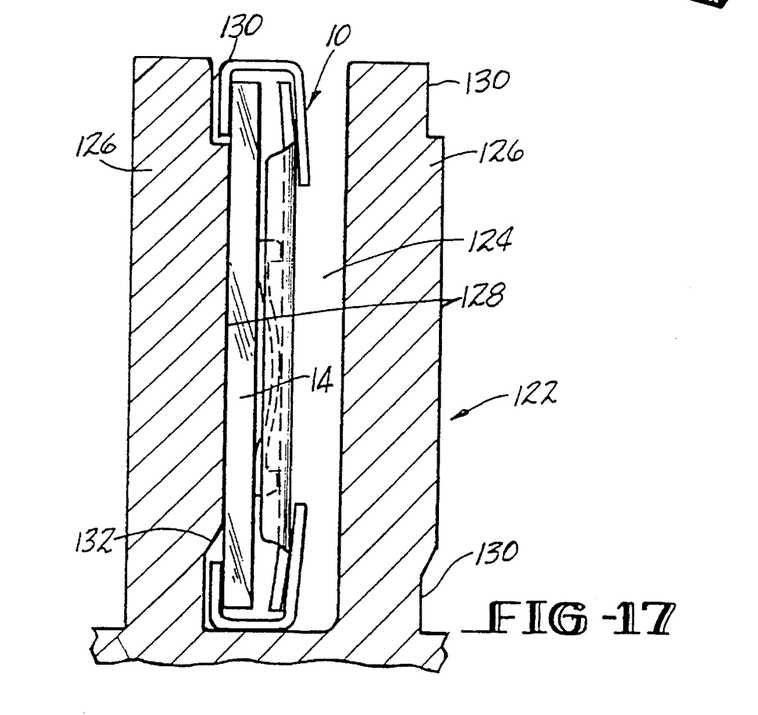
FIG. 17 is an enlarged partial sectional view of the heat exchanger block of the thermal cycler shown in FIG. 16.

FIG. 17 is a partial section of the block 122 through a slide assembly 10 mounted on edge in one such slot 124. The top edge 132 of the bottom groove 130 is smoothly chamfered to prevent its catching on the clip 28 as the slide 14 is removed vertically. For a similar reason, the upper groove 130 does not have an upper edge. Naturally, when slides are mounted in this manner, we cannot rely upon gravity to hold the glass slide 14 against the flat metal heat exchange surface 128. Therefore, small leaf springs of conventional design (not shown in the drawing) may be placed at the ends of each slot 124 to hold the slide gently but firmly against the vertical metal surface 128. Once again, mineral oil, grease, ethylene glycol or other thermally conductive liquid should be used between the slide 14 and the flat metal heat exchange surface 128 to maximize the heat transfer. The springs may be engaged after the slides are loaded and disengaged before their removal or may be permanently mounted in the slots 124 so as to continuously press the slide 14 assembly 10 into engagement with surface 128.

When thermal cycling is completed, the assembled slides 10 are removed from their slots 124 for further analysis. The containment system parts are easily removed by sliding the clips 28 off of the slide 14. If the containment parts and the slide 14 are dropped into a container of 5% bleach to sterilize them, then later rinsed and dried, they can be reused many times. The limit on reuse will be determined by deterioration of the cover 16 and/or rim 19, a condition that is very easily checked by a visual examination, before or after the cover 16 is clamped to a slide 14. Note that unlike PCR performed on a sample in solution, contamination with unwanted DNA is far less of a problem with in situ PCR. The reason is that the contaminating DNA does not get inside properly fixed cells. Further, any contaminating DNA is washed away with the reagents, before the development steps after thermal cycling. This fact about in situ PCR makes washable and re-usable parts more acceptable than they would be for PCR in solution.

Reagent for In Situ PCR

In our work, we found that the optimum reagent quantities for in situ PCR are different than for PCR in solution. First, there is the problem of surface to volume ratio. Ten microliters of reagents in a MicroAmp™ tube has a surface touching the container of about 17 mm². The same volume of reagent between a slide 14 and a cover 10 mm in diameter has about 157 mm², i.e. about 9 times greater. Therefore, any effects hostile to the PCR caused by surface conditions, such as absorption of polymerase enzyme, are exaggerated in the in situ case. If the surfaces are more hostile than the carefully chosen polypropylene material of PCR reaction tubes, the hostile effects are very greatly exaggerated, and can easily kill the PCR completely. The widely used silane-treated glass slide is a surface substantially more hostile than polypropylene, for example.

We found that to get successful amplification of PCR in solution in containments in accordance with the invention of PCR reagents against a silanized slide, we needed to increase the amount of Taq polymerase in the reaction, from 2.5 units per 100 µl typical of PCR in solution to 12.5 units per 100 µl. We also found that adding 1 mg/ml of bovine serum albumen (BSA) to the reagent protected the PCR from the slide surface. We believe the BSA acts by promptly forming at least a monolayer of protein over all the surface it touches. Thus, monolayer presents a surface to which Taq polymerase enzyme does not strongly adhere.

We have already discussed the loss of water from the reaction during cycling. In spite of care and speedy work, some will be lost during hot start loading. Also some moisture is lost by diffusion into or even through the thin walls of the compliant rubber or plastic cover 16. In view of these small additional losses, the formulation of a PCR reagent for in situ amplification should be at the most dilute end of the optimum range of concentrations for each component because the only change in concentrations during loading and cycling, if any, is likely to be a very small increase due to loss of water.

Thus, the complete in situ PCR system includes the slide and containment system 10, the assembly fixture 40 or 80, a modified thermal cycler designed for one or more slides 14 with the containment assembly 10 attached, and reagents 13 modified as described above. The novel and unexpected result of this combination is convenient, robust and sensitive detection and location of specific DNA sequences within cells and tissue specimens.

If lateral positioning or spacing of the sample 12 between the edges of the slide 14 is constant, the ring 20 may be integrated into the cross beam 22. This will simplify component construction and assembly of the retaining assembly 18 and the containment system 10.

Figure 18:
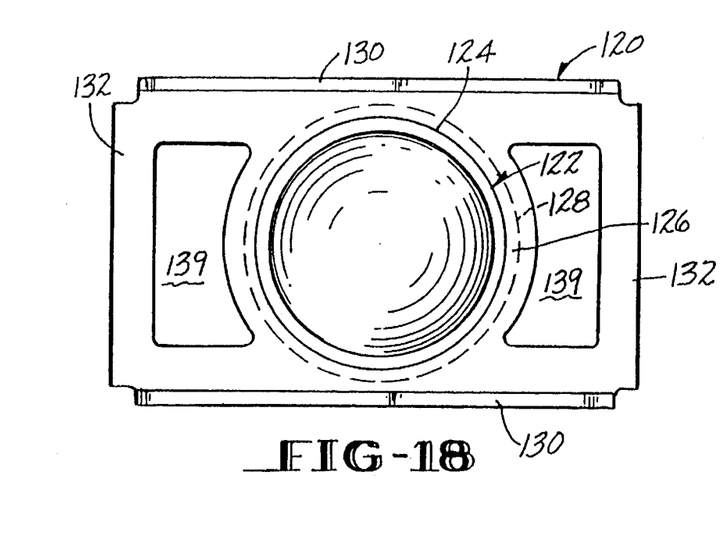
FIG. 18 is a top view of a first alternative embodiment of the cross beam and cover in accordance with the invention.
Figure 19:
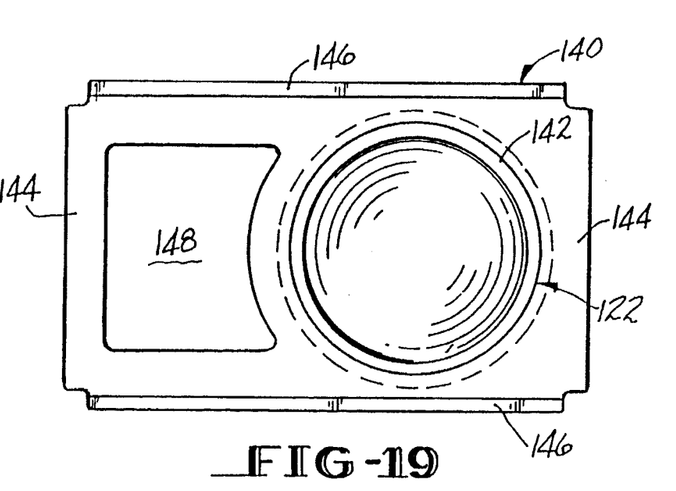
FIG. 19 is a top view of a second alternative embodiment of the cross beam and cover in accordance with the invention.

Construction of the containment system 10 may be simplified in several ways. For example, the cross beam and retaining ring may be integrated. A first alternative embodiment of the cross beam and cover in accordance with the invention is illustrated in FIG. 18. A variation on this alternative cross beam is illustrated in FIG. 19. Like numbers will be utilized in the following description to describe identical or interchangeable components in the in situ PCR containment system described above.

Figure 20:
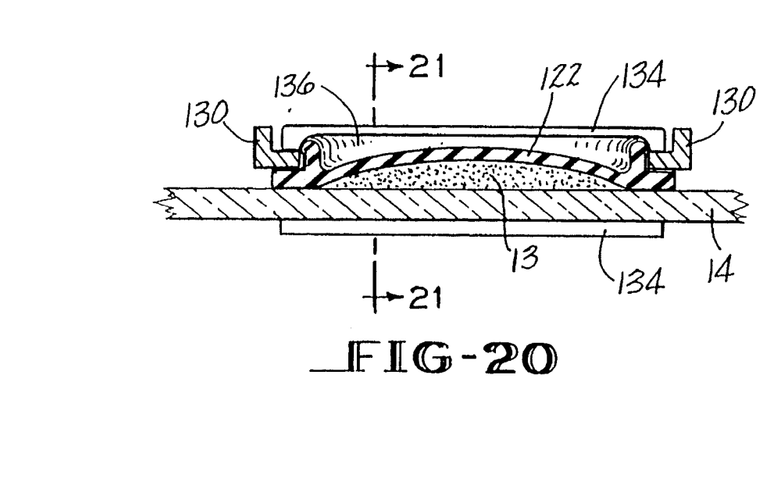
FIG. 20 is a sectional view of the assembled containment system in accordance with the invention incorporating an alternative cross beam and the alternative cover shown in FIGS. 18 and 19.

Referring now to FIGS. 18 and 19, top views of alternative cross beams 120 and 140 are each shown assembled to an alternative cover 122. The difference between the cross beams 120 and 140 is simply the placement of the circular aperture 124 and 142. The aperture 124 in cross beam 120 is centrally located. In contrast, the aperture 142 in cross beam 140 is located adjacent to one end 144 of the cross beam 140. The combination of the two cross beams 120 and 140 permits the placement of the cover 122 over a sample 12 mounted anywhere on a slide 14 merely by changing the orientation of the cross beam 140 or by choosing the cross beam 120 which has a centrally disposed aperture 124. In these embodiments, the seal ring is integral with the cross beam. Cross beam 120 has a generally circular ring portion 126 which presses on a rim portion 128 of the cover 122 when the containment system 10 is assembled as shown in the partial sectional views of FIGS. 20 and 21.

Figure 21:
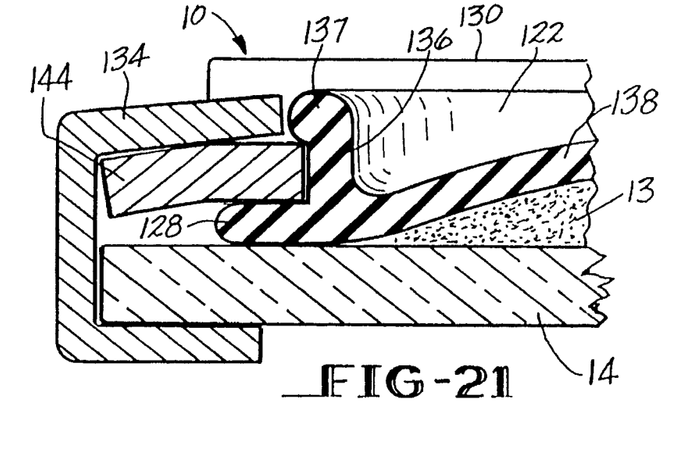
FIG. 21 is an enlarged partial sectional view of the containment system shown in FIG. 20 taken along the line 21—21.

The cross beam 120 is preferably a stamped piece from a sheet of stainless steel. The cross beam 120 has a pair of parallel, vertically bent edges forming rails 130 extending between opposite ends 132 which are bent downwardly at a shallow angle of about 3° to receive the clips 134 in a manner similar to clips 28 in the first embodiment described above. As shown in FIG. 21, each clip 134 squeezes the end 132 and glass slide 14 together during installation to compress the rim portion 128 of the cover 122 to the slide 14.

An especially unique feature of this alternative embodiment of a cross beam 120 and cover 122 arrangement is that the cover 122 has an annular rib or ridge 136 between the rim portion 128 and the central domed or concave portion 138 under which the reagent mixture 13 is retained. This annular ridge 136 preferably has an enlarged bulbous top 137 which snap fits into the aperture 124 retaining the pieces together. The cover 122 and the cross beam 120 may be assembled as a separate unit to simplify the final assembly of the components of the containment system 10 of this alternative embodiment as shown in FIG. 21.

The cross beam 120 may have cutout regions 139 which eliminate unnecessary metal material. Alternatively, these cutout regions 139 may be replaced by ribs or corrugations (not shown) to enhance rigidity of the cross beam 120.

Referring now to FIG. 19, cross beam 140 has parallel raised rail edges 146 and a single cutout area 148 in contrast to the two cutout areas in the cross beam 120. The cross beam 140 may be rotated 180° from that shown in FIG. 19 for placement on a slide 14 so that the combination of one cross beam 140 and one cross beam 120 permits coverage of practically all potential sample locations on a slide 14.

Assembly of the alternative containment system 10 as shown in FIGS. 18–21 is similar to that above described for the first embodiment except that a retaining ring 20 is no longer required and the cover 122 and cross beam 120 are assembled together first. The manual or mechanically assisted assembly tools 40 and 80 may be utilized as previously described to assemble the containment system to the slides and perform hot starts.

Figure 22:
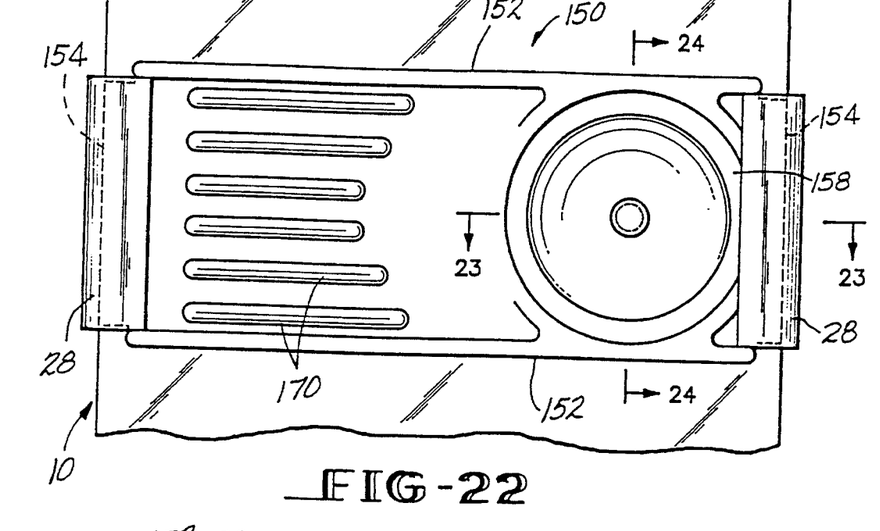
FIG. 22 is a top view of a containment system assembled to a slide in accordance with the invention utilizing a third alternative preferred embodiment of the cross beam and cover.
Figure 23:
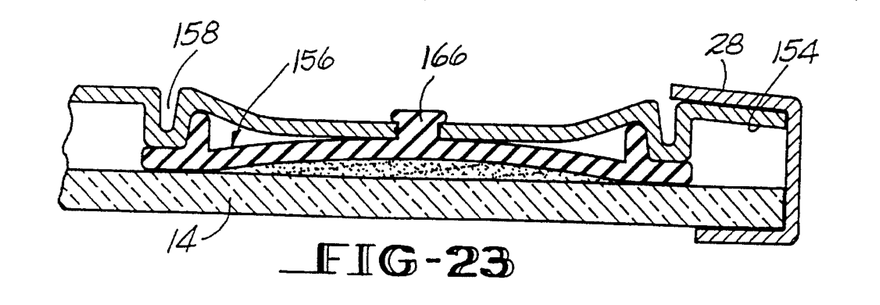
FIG. 23 is a partial sectional view of the invention shown in FIG. 22 taken on the line 23—23.
Figure 24:
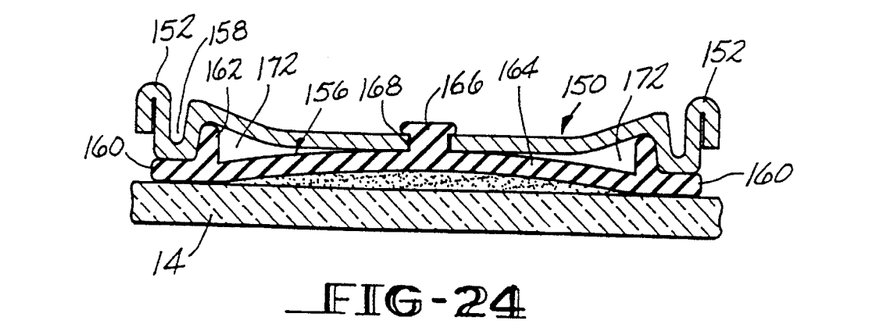
FIG. 24 is a partial sectional view of the invention shown in FIG. 22 taken along the line 24—24.

FIGS. 22 through 24 show a third embodiment of the containment system 10 in accordance with the present invention utilizing another alternative cover and cross beam 150. The cross beam 150 in this embodiment, shown in a top view in FIG. 22, is again a stamped sheet metal piece having parallel raised rails 152 and bent ends 154. However, this embodiment does not have a central aperture through which the central portion of the cover 156 extends. Instead, an annular trough or depression 158 in the sheet metal cross beam 150 performs the function of the retaining ring 20 in the first embodiment and the ring portion 126 in the second embodiment. This annular trough 158 is sized so that the rim portion 160 of the cover 156 is fully engaged with the underside of the trough 158. As in the cover of the second embodiment, a raised ridge 162 projects upward between the rim portion 160 and a central portion 164 of the cover 156. The cover 156 may optionally include a central protrusion or knob 166 which is designed to snap fit into an opening 168 centrally disposed inside the annular trough 158 to retain the cover 156 and cross beam 150 together. If this central protrusion 166 is provided as shown, it is not necessary to provide the ridge 162 on the cover 156. In addition, it is not necessary to mold the cover 156 with a concave central portion 164. The snap fit of the protrusion 166 into the opening 168 pulls the central portion up against the central portion of the cross beam 150 to product the required curvature for accommodating the reagent 13. Although the ridge 162 is not required in this case, the ridge 162 may help define this central curvature.

The cross beam 150 may also have a plurality of corrugations or ribs 170 as shown in FIG. 22, pressed into the sheet metal material to increase the rigidity of the structure so that it can be fabricated of very thin sheet metal material, thus reducing its thermal mass and overall thickness.

This alternative third embodiment 150 has a distinct advantage over the embodiments previously described. As the cross beam 150 completely covers the compliant cover 156, the requirement that the cover material be impervious to diffusion of moisture as well as being non-hostile to the PCR reaction is greatly reduced. Accordingly, this permits a broader selection of materials. For example, the cover 156 may be a single molded body of silicone rubber. A composite or sandwich of the silicone rubber with a nonpermeable elastomer such as polypropylene is not required. This feature results because the diffusion of moisture through the central portion 164 of the cover 156 into the closed space 172 quickly reaches equilibrium because the volume is very small. Evaporation can be further minimized by eliminating the optional protrusion 166 and the optional opening 168 shown. If the central knob 166 is eliminated, then the raised ridge 162 may be used to temporarily fasten the cover 156 in place on and under the cross beam 150.

The void region 172 is necessary, however, to permit displacement of the cover 156 during compression of the rim portion 160 during installation of the clips 28 or 134 to provide the seal to effectively retain the reagent 13 against the sample 12. The trapped volume 172 also serves to control the pressure under the cover 156 during thermal cycling. This reduces or may prevent bubble formation in the reagent 13 during incubations at the denaturation temperature near 95° C.

The formation of the rails 152 is best shown in the partial sectional view of FIG. 24. These parallel rails 152 are essentially doubled over edges of the sheet metal piece forming the cross beam 150. This design is relatively rigid and permits use of sheet material of minimal thickness. In addition, the doubled over edges minimize the presence of sharp edges which could be a handling hazard with thin metal materials. The ends 154 may also be bent over as are the rails 152 for this same reason.

The cross beam 150 may have the annular trough 158 centrally disposed to accommodate centrally located samples on the slide 14. This alternative is not illustrated as it is an obvious variation from that shown in FIG. 22.

While the above description is illustrative of the preferred embodiments of the present invention, it will be appreciated that the inventive concept of an in situ PCR containment system in accordance with the invention may be practiced otherwise than as specifically described. For example, the cross beams and dips may be made of a rigid plastic material or one of the clips 28 may be made an integral part of one end of the cross beam 22 so that only one clip 28 is needed to fit over the opposite end 26 of the cross beam 22. Thus the embodiments of the invention are subject to modification, variation, and change without departing from the proper scope and fair meaning of the appended claims. Accordingly, it is intended to embrace all such changes, modifications, and variations that fall within the spirit and broad scope of the appended claims. All patent applications, patents and other publications cited herein are incorporated by reference in their entirety.

What is claimed is:

1. An apparatus for assembly of an in situ PCR sample and reagent fluid containment system on a glass slide wherein said containment system comprises a cover member and a retaining assembly, said apparatus comprising:

a base;

a support post mounted on said base, said support post having a generally horizontal top surface for receiving and supporting components of said retaining assembly in a predetermined spaced relation;

a vertically movable glass slide support platen movable between a position above said top surface of said post and a position wherein portions of said platen are adjacent said top surface of said post;

an elongated compression arm movably supported from said base at a position spaced from said post, said arm being operable to engage a glass slide placed in said support platen and lower said platen and slide until said slide engages said retaining assembly; and a spring biased retaining assembly installation mechanism pivotally attached to said post, said mechanism having a pair of pliers having finger portions positioned adjacent and above opposite edges of said horizontal top surface of said post operable to move said finger portions toward each other.

2. The apparatus according to claim 1 wherein said installation mechanism further comprises each of said pliers having a handle portion extending from each of said finger portions, each of said pliers being pivotally mounted to said post.

3. The apparatus according to claim 2 wherein said handle portions each wrap around at least a portion of two sides of said post.

4. The apparatus according to claim 1 wherein said compression arm has an aperture therethrough aligned over said support post.

5. The apparatus according to claim 4 wherein said arm has a cushioning pad around said aperture for contacting said glass slide.

* * * * *